US012636070B2

(12) United States Patent (10) Patent No.: US 12,636,070 B2

Nagtegaal (45) Date of Patent: May 26, 2026

(54) HANDLE FOR A SURGICAL INSTRUMENT

(71) Applicant: GYRUS ACMI, INC, Bartlett, TN (US)

(72) Inventor: Marno Nagtegaal, St Mellons (GB)

(73) Assignee: GYRUS ACMI, INC, Westborough, MA (US)

( * ) Notice: Subject to any disclaimer, the term of this patent is extended or adjusted under 35 U.S.C. 154(b) by 824 days.

(21) Appl. No.: 17/868,052

(22) Filed: Jul. 19, 2022

(65) Prior Publication Data

US 2023/0078434 A1 Mar. 16, 2023

Related U.S. Application Data

(60) Provisional application No. 63/243,499, filed on Sep. 13, 2021.

(30) Foreign Application Priority Data

Sep. 14, 2021 (GB) ...................................... 2113073

(51) Int. Cl.
| | |
|---|---|
| *A61B 18/14* | (2006.01) |
| *A61B 17/00* | (2006.01) |
| *A61B 17/29* | (2006.01) |

(52) U.S. Cl.
CPC ...... *A61B 18/1445* (2013.01); *A61B 18/1442* (2013.01); *A61B 2017/00438* (2013.01); *A61B 2017/2939* (2013.01)

(58) Field of Classification Search
CPC ............ A61B 17/2841; A61B 18/1442; A61B 18/1445; A61B 2017/00424;

(Continued)

(56) References Cited

U.S. PATENT DOCUMENTS

| | | |
|---|---|---|
| 5,234,460 A | 8/1993 | Stouder, Jr. |
| 5,472,451 A | 12/1995 | Freitas et al. |

(Continued)

FOREIGN PATENT DOCUMENTS

| | | |
|---|---|---|
| DE | 102007016498 A1 | 10/2008 |
| DE | 202016103085 U1 | 6/2016 |

(Continued)

OTHER PUBLICATIONS

Jan. 6, 2022 Combined Search and Examination Report issued in British Patent Application No. 2113073.7.

(Continued)

*Primary Examiner* — Tigist S Demie

(74) *Attorney, Agent, or Firm* — Schwegman Lundberg & Woessner, P.A.

(57) ABSTRACT

A surgical instrument with a handle for a surgical instrument is provided, comprising a first arm and a second arm, wherein at least one of the arms being movable with respect to the other between an open and closed position. An end effector such as a pair of opposing jaws for grasping tissue may be disposed at the distal end of the two arms. At the proximal end of each arm is a finger loop, or some other suitable means for holding by the handle, which are used to actuate the arms between the open and closed position. At least one of the finger loops is arranged to pivot about the longitudinal axis of the arm from which it extends, for example, the finger loop may be connected to the arm by a hinged connection, or any other suitable connection for enabling the finger loop to be pivotably rotated.

19 Claims, 3 Drawing Sheets

(58) Field of Classification Search
CPC .... A61B 2017/00438; A61B 2017/291; A61B
2017/2911; A61B 2017/2939; A61B
2018/00607; A61B 2018/1455
See application file for complete search history.

(56) References Cited

U.S. PATENT DOCUMENTS

| | | | |
|---|---|---|---|
| 2007/0299469 A1 | 12/2007 | Carpenter et al. | |
| 2012/0209254 A1* | 8/2012 | Park | A61B 17/2909 |
| | | | 606/1 |
| 2015/0335347 A1 | 11/2015 | Hirai et al. | |
| 2016/0151110 A1* | 6/2016 | Kerr | A61B 18/1442 |
| | | | 606/45 |
| 2022/0175408 A1* | 6/2022 | Lee | A61B 17/29 |

FOREIGN PATENT DOCUMENTS

| | | | |
|---|---|---|---|
| EP | 0827715 A2 | 3/1998 | |
| GB | 2460392 A | 12/2009 | |

OTHER PUBLICATIONS

Mar. 5, 2024 Examination Report issued in British Patent Application No. GB2113073.7.
Jan. 29, 2024 Office Action issued in British Patent Application No. GB2113073.7.

* cited by examiner

FIG. 2A                    FIG. 2B                    FIG. 2C

HANDLE FOR A SURGICAL INSTRUMENT

TECHNICAL FIELD

Embodiments of the present invention described herein relate to a handle arrangement for a surgical instrument, and in particular a handle arrangement comprising moveable arms.

BACKGROUND AND PRIOR ART

It is known to provide a surgical instrument with a pair of opposing jaw members configured to grasp tissue therebetween. In known arrangements, the finger loops are static, or fixed. The finger loops are thus sized such that they can accommodate the thumbs of the majority of the population. This ensures that the most medical professionals are able to use a standardised, mass-produced instrument.

In such instruments, users with smaller thumbs may experience difficulty maintaining their thumbs within the finger loops as there is too much clearance. Furthermore, users with larger thumbs may experience discomfort due to increased friction within the finger loops.

In order to maintain the advantages of standardised manufacture for surgical instruments while mitigating the problems of known finger loop designs, improved design for finger loops is required.

SUMMARY OF THE INVENTION

Embodiments of the present disclosure provide an improved surgical instrument having advantages over the prior art.

In particular, the present disclosure provides a handle for a surgical instrument comprising a first arm and a second arm, wherein at least one of the arms being movable with respect to the other between an open and closed position. An end effector such as a pair of opposing jaws for grasping tissue may be disposed at the distal end of the two arms. At the proximal end of each arm is a finger loop, or some other suitable means for holding by the handle, which are used to actuate the arms between the open and closed position. At least one of the finger loops is arranged to pivot about the longitudinal axis of the arm from which it extends, for example, the finger loop may be connected to the arm by a hinged connection, or any other suitable connection for enabling the finger loop to be pivotably rotated. In doing so, the amount of friction on the thumb and index finger during operation is reduced, thereby provided a more ergonomic handle compared to those with static finger loops. Additionally, the finger loops fit users of different sizes more comfortably as excess clearance is taken up when the finger loop pivots to rest on the thumb or index finger.

A first aspect provides a handle for a surgical instrument, comprising: a first arm and a second arm, each comprising a proximal end and a distal end and defining a longitudinal axis, at least one of the first and second arms being movable with respect to the other between an open position, in which the first and second arms are spaced one from another, and a closed position, in which the first and second arms are brought closer together; and an actuation means arranged at the proximal end of at least one of the first and second arms for moving the first and second arms between the open and closed positions; characterised in that the actuation means is further arranged to pivot about the longitudinal axis of the arm on which it is arranged.

The actuation means may be arranged to pivot by means of a hinged connection.

The actuation means may comprise a finger loop. It will of course be appreciated that any suitable means for enabling a user to grasp the handle may be used.

The actuation means may be arranged at the proximal end of the first arm and the second arm.

The actuation means may be configured to pivot about the longitudinal axis in both the clockwise and the anticlockwise direction. In doing so, the handle can be comfortably operated by both right-handed and left-handed users.

The actuation means may be configured to pivot about the longitudinal axis of the arm within a fixed range of motion. This prevents the actuation means from spinning and thus allows users to quickly get their hands into a comfortable position, which may be particularly important during surgery if a user needs to change between hands whilst holding tissue between the end effector located at the end of the two arms. For example, the fixed range of motion may be between 90 degrees and −90 degrees. Alternatively, the fixed range of motion may be between 60 degrees and −60 degrees. As another example, the fixed range of motion may be between 45 degrees and −45 degrees. Alternatively, the fixed range of motion may between 30 degrees and −30 degrees. It will of course be appreciated that any suitable range of motion may be provided.

The actuations means arranged at the proximal end of the first arm may pivot between a first fixed range of motion. The actuation means arranged at the proximal end of the second arm may pivot between a second fixed range of motion. For example, the first fixed range of motion or the second fixed range of motion may be between 60 and −60 degrees, or as an alternative example, the first fixed range of motion or the second fixed range of motion may be between 45 and −45 degrees, or as a further example, the first fixed range of motion or the second fixed range of motion may be between 30 and −30 degrees.

It will of course be appreciated that first fixed range of motion may be different to or the same as the second fixed range of motion.

A switch mechanism may be located on the handle, comprising: an activation button operable to deliver a source of radio frequency (RF) energy to an end effector disposed on the distal end of at least one of the first and second arms; and a protrusion operable to compress the activation button.

The switch mechanism may be arranged on the handle such that, the activation button is configured to be activated by one of the first and second arms when the handle is in the closed position.

A second aspect provides a surgical instrument, comprising: an end effector; and a handle for actuating the end effector according to the first aspect.

The end effector may comprise a first jaw member disposed on the distal end of the first arm and a second jaw member disposed on the distal end of the second arm. In this respect, moving the first and second arms to the closed position causes the first and second jaw members to move to a closed position such that tissue can be grasped therebetween.

A third aspect provides an electrosurgical system, comprising: an RF electrosurgical generator; and a surgical instrument according to the second aspect.

There may be provided a method of using a surgical instrument comprising the handle described herein. The method may involve performing surgery on a human or animal patient using the surgical instrument. The method may include one or more steps of operating the actuation means so as to move the first and second arms between the open and closed positions so as to move the end effector between first and second conditions to thereby perform a surgical step. The end effector may be a pair of opposing jaws, such that moving the first and second arms to the closed position moves the pair of opposing jaws to a closed position to thereby grasp tissue therebetween.

BRIEF DESCRIPTION OF THE DRAWINGS

Embodiments of the disclosure will now be further described by way of example only and with reference to the accompanying drawings, wherein like reference numerals refer to like parts, and wherein.

DETAILED DESCRIPTION OF THE EMBODIMENTS

Figure 1:
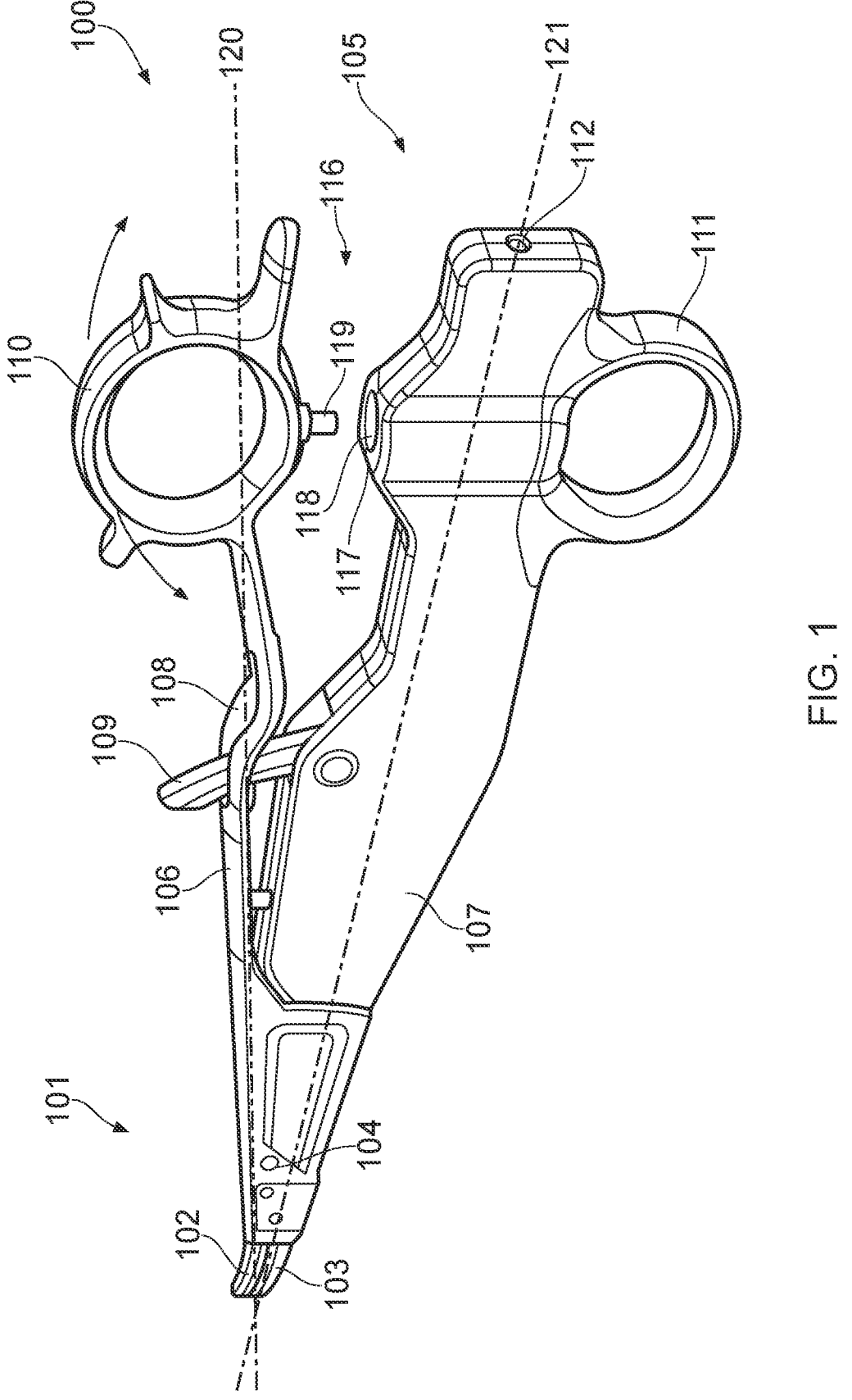
FIG. 1 is a perspective view of a surgical instrument according to an embodiment of the present disclosure, shown in a closed configuration.

FIGS. 1 and 2A-2C illustrate a surgical instrument 100 according to an embodiment of the present disclosure.

At the distal end of the instrument 100, the instrument 100 comprises an end effector 101 comprising a first jaw member 102 and second jaw member 103, thereby defining a pair of opposing jaws. The end effector 101 may be curved. At least one of the jaw members 102, 103 is moveable relative to the other between a first open position in which the jaw members 102, 103 are disposed in a spaced relation relative to one another, and a second closed position in which the jaw members 102, 103 cooperate to grasp tissue therebetween. In some cases, the jaw members 102, 103 may be capable of being connected to a source of electrical energy such that the jaws are capable of conducting energy through tissue held therebetween to affect a tissue cut, seal or coagulate, To affect this, the jaw members 102, 103 may comprise one or more electrodes (not shown) arranged on or as the inner opposed surfaces of the jaw members 102, 103 and which in use have connections to receive an electrosurgical radiofrequency (RF) signal for the sealing or coagulation of tissue.

At the proximal end of the instrument 100, the instrument 100 comprises a handle 105. The handle comprises a first, upper arm 106 and a second, lower arm 107. The upper arm 106 extends from the proximal end of the first, upper jaw member 102 and the lower arm 107 extends from the proximal end of the second, lower jaw member 103.

The proximal end of the handle 105 may include a mechanism for actuating each arm 106, 107. The actuating mechanism depicted in FIG. 1 is a pair of finger loops 110, 111. The first, upper finger loop 110 may extend from the proximal end of the first, upper arm 106. The second, lower finger loop 111 may extend from the proximal end of the second, lower arm 107.

The distal ends of the two arms 106, 107 are pivotally coupled together through the central or main pivot 104. As such, when the arms 106, 107 are moved relative to each other between a first, open position, in which the arms 106, 107 are disposed in a spaced relation relative to one another, and a second, closed position, this movement causes a corresponding opening and closing of the jaw members 102, 103.

The proximal end of the surgical instrument 100 may also be further provided with a switch mechanism shown generally at 116. The switch mechanism 116 may comprise an activation button 118 or similar located in a recess 117 disposed on one of the arms. The switch mechanism further comprises a corresponding protrusion 119 on the opposite arm. In the example illustrated, the recess 117 is located on an upper surface of the lower arm 107, whilst the protrusion is located on a lower surface of the upper arm 106.

When the arms 106, 107 are in a closed configuration, the finger loops 110, 111 can be brought together such that the activation button 118 is activated by the protrusion 119 to thereby deliver electrical energy to the jaw members 102, 103. It will be appreciated that the recess 117 and the activation button 118 may be located on the upper arm 106, with the protrusion 119 being located on the lower arm 107.

Due to the pivotable finger loops 110, 111 explained further below, the recess 117 and the button 118 are sized such that the protrusion 119 may be received in the recess 117 from a broad range of angles. For example, it is preferable that the recess 117 and the button 118 comprise a larger surface area than that of the protrusion 119.

The first jaw member 102, the first arm 106 and the first finger loop 110 define a first longitudinal axis 120 therethrough. Similarly, the second jaw member 103, the second arm 107 and the second finger loop 111 define a second longitudinal axis 121 therethrough.

At least one of the finger loops 110, 111 may be configured to pivot about their respective longitudinal axis. In the example of FIG. 1, the first finger loop 110 is configured to pivot about the first longitudinal axis 120 whilst the second finger loop 111 is fixed. The person skilled in the art would appreciate that, alternatively, the second, lower finger loop 111 may be configured to pivot about the second longitudinal axis 121. In some embodiments, both of the first finger loop 110 and the second finger loop 111 may be configured to pivot about their respective longitudinal axis 120, 121. This configuration is advantageous, being more ergonomic than static finger loops as the amount of friction on the thumb and index finger during operation is reduced, and thus the amount of sliding of a user's fingers within the loops will be reduced. Additionally, the finger loops 110, 111 can be made slightly smaller in height, and thereby fit users of different sizes more comfortably as excess clearance is taken up when the finger loop pivots to rest on the thumb or index finger.

Whilst FIG. 1 illustrates the surgical instrument with the upper finger loop 110 configured to pivot, the person skilled in the art would appreciate that both of the finger loops 110, 111 may be configured to pivot. Surgical instruments with a curved end effector, such as the end effector 101 illustrated in FIG. 1, are required to be inverted in order to change the orientation of the curvature. That is, the instrument would be turned upside-down such that the first finger loop 110 is positioned as the lower finger loop, and the second finger loop 111 is positioned as the upper finger loop. An instrument comprising a pair of finger loops which are both configured to pivot enables standardised manufacture which caters to users of either handedness and facilitates seamless inversion of the surgical instrument. The finger loop 110 may be coupled to the first arm 106 by a hinged connection (not shown), or any other suitable connection for allowing the finger loop 110 to be rotated about its longitudinal axis.

The finger loops 110, 111 may be configured to pivot in either of a clockwise or an anticlockwise direction about their respective longitudinal axis 120, 121. This is advantageous as the handedness of the user will affect the direction in which the finger loops 110, 111 pivot and thus instruments can be made to be used by users of both left-handedness and right-handedness.

Figure 2:
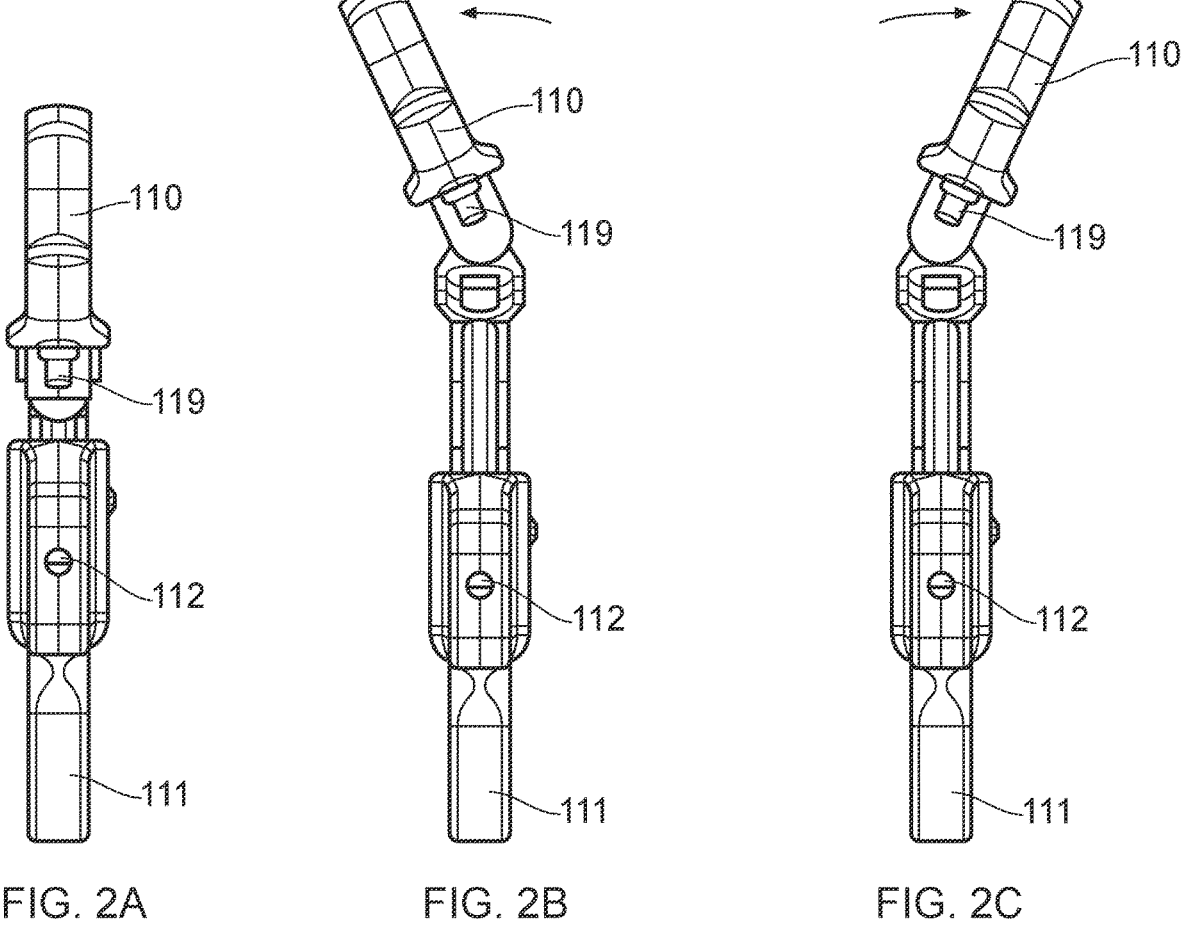
FIG. 2A is a rear view of the proximal end of the surgical instrument of FIG. 1, shown in the closed configuration.
FIGS. 2B and 2C are rear views of the proximal end of the surgical instrument of FIG. 1, shown in the open configuration, with the actuation means pivoted in the clockwise and anticlockwise directions.
Figure 3:
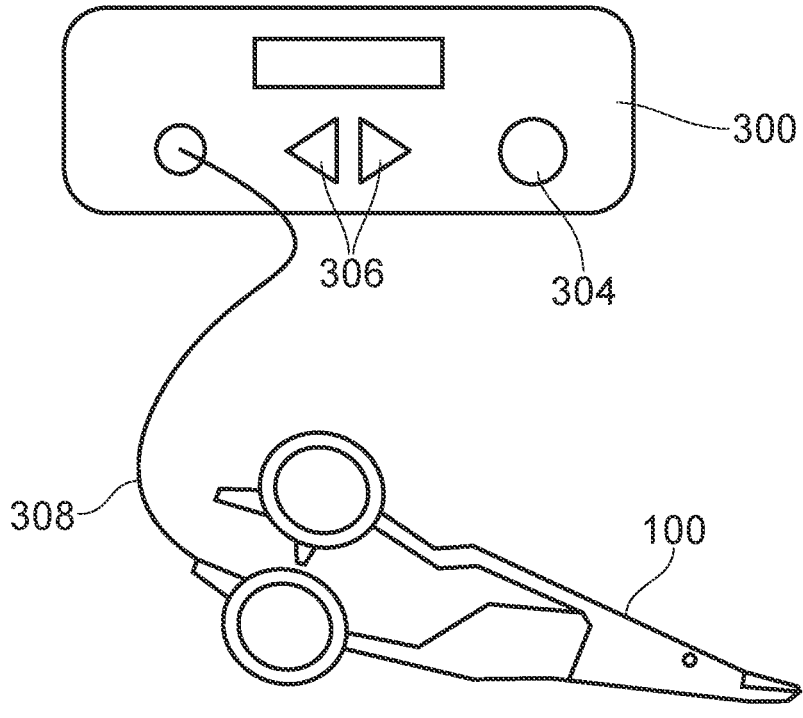
FIG. 3 is a representation of an electrosurgical system including a generator and an instrument in accordance with embodiments of the disclosure.

Turning to FIGS. 2A-2C, for example, a user operating the instrument 100 with their right hand and actuating the arms from a closed position to an open position would operate the first, upper finger loop 110 with their thumb and operate the second, lower finger loop 111 with their index finger. In the embodiment depicted in FIG. 1, the upper finger loop 110 is configured to pivot whilst the lower finger loop 111 is static. During operation, the upper finger loop 110 would pivot about the longitudinal axis 120 during use. When operated by a right hand, the upper finger loop 110 would pivot clockwise during use when viewed from the rear of the instrument as best seen in FIG. 2C. Alternatively, for a user operating the instrument 100 with their left hand and actuating the arms from a closed position to an open position, the upper finger loop 110 would pivot anti-clockwise when viewed from the rear of the instrument as best seen in FIG. 2B.

The finger loops 110, 111 may be configured to pivot within a fixed range of motion. That is, the finger loops 110, 111 may be configured to rotate between limited angles. This is advantageous as the finger loops are prevented from spinning when users are trying to engage them and allows users to engage the finger loops more quickly.

Specifically, either of the fingers loops 110, 111 may be configured to pivot between 60 and −60 degrees, that is to say, 60 degrees in the clockwise and anti-clockwise direction. Designing the finger loops to pivot between these angles gives the optimum range of sizing adjustment, as the clearance in the finger loops can be reduced by increased rotation during use. The finger loops 110, 111 may otherwise be configured to pivot between 30 and −30 degrees, that is, 30 degrees in the clockwise and anti-clockwise direction. A narrower range of motion such as this one may provide a more stable operation by a user as it rotates less when being engaged. Alternatively, either of the finger loops 110, 111 may be configured to pivot between 45 and −45 degrees, that is, 45 degrees in the clockwise and anti-clockwise direction.

For configurations in which the finger loops 110, 111 are each configured to pivot, the range of motion for the upper finger loop 110 may be different to the range of motion for the lower finger loop 111. For example, the upper finger loop 110 may be configured to pivot between 60 and −60 degrees and the lower finger loop 111 may be configured to pivot between 45 and −45 degrees, or vice versa. As another example, the upper finger loop 110 may be configured to pivot between 45 and −45 degrees and the lower finger loop 111 may be configured to pivot between 30 and −30 degrees, or vice versa. As a further example, the upper finger loop 110 may be configured to pivot between 30 and −30 degrees and the lower finger loop 111 may be configured to pivot between 15 and −15 degrees, or vice versa.

It will of course be appreciated, however, that the range of motion of either of the finger loops 110, 111 may be fixed at any suitable angle between 90 degrees in the clockwise direction and 90 degrees in anti-clockwise direction. Likewise, in cases where both finger loops 110, 111 both configured to pivot, they may be provided with the same or a different fixed range of motion.

The electrosurgical instrument 100 may also include a mechanical cutting blade (not shown) coupled to a blade actuator, such as a blade trigger 109, which protrudes from the second, lower arm 107. The cutting blade may be disposed within one of the arms 106, 107 such that actuation of the blade trigger 109 translates the cutting blade along the respective arm 106, 107 and between the two jaw members 102, 103 to thereby cut any tissue grasped therebetween. The first, upper arm 106 may be further provided with a slot 108 therein between the proximal end and the distal end. The slot 108 may be configured to receive the blade trigger 109. It will be understood that the slot 108 may instead be provided on the upper arm 107 whilst the blade trigger 109 may instead be provided on the upper arm 106.

Referring now to Figure the instrument 100 in use is intended for connection to an electrosurgical generator 300 having a controllable RF source therein (not shown) that in use produces an RF coagulation signal that coagulates or seals tissue when applied thereto via the electrodes of the end effector of the instrument 100 and/or an RF cutting signal that cuts the tissue when applied thereto via the electrodes of the end effector of the instrument 100. Electrosurgical generator 300 includes control input switches 304 and 306, to respectively allow the generator to be turned on and off, and to allow the power of the RF coagulation or cutting signal fed to the instrument 100 to be controlled.

In use, the instrument 100 is connected to generator 300 by control and power line 308, which contains separate electrical lines to allow an RF signal to be fed to the end effector of the instrument 100 via internal wiring, and to allow a control signal to be received from the activation button 118 of the instrument 100, to command the electrosurgical generator to output an RF coagulation or cutting signal to the instrument 100. The power lines 308 connect to the instrument 100 through a port 112, which is illustrated in FIG. 1 and FIGS. 2A-2C as an aperture in the proximal end of the lower arm 107. In use, the surgeon activates the generator via on-off switch 304 and selects the cutting, coagulation or sealing signal strength to be generated by the internal RF source using buttons 306. During a surgical procedure with the instrument when a cutting or coagulation RF signal is required at the end effector 101, the surgeon controls the generator to produce such a signal by pressing the activation button 118 on the instrument, the generated RF signal then being passed via the electrical lines 308 to the end effector. That is, pressing of the activation button 118 in use causes an RF coagulation or cutting signal to be supplied to the appropriate electrodes contained within the end effector.

The jaw members 102, 103 may each have an electrode or conductive pad. In such cases, the conductive pad of the upper jaw member 102 and the conductive pad of the lower jaw member 103 are electrically coupled to the electrosurgical generator 300 via wires and connectors to supply RF energy to tissue grasped between the conductive pads. The conductive pads are arranged to have opposed polarity. Wires and associated connections may extend from the activation button 118 through the upper arm 106 and/or the lower arm 107 to the upper and lower jaw members 102, 103 and the respective connections to the upper and lower electrodes. The activation button 118 may complete a circuit when actuated by electrically coupling at least two leads together. As such, an electrical path is then established from an electrosurgical generator 300 to an actuator to supply RF energy to the instrument 100.

Various modifications whether by way of addition, deletion, or substitution of features may be made to abovedescribed embodiments to provide further embodiments, any and all of which are intended to be encompassed by the appended claims.

The invention claimed is:

1. A handle for a surgical instrument, comprising:
a first arm and a second arm, each comprising a proximal end and a distal end having a respective jaw member disposed thereon, and defining a longitudinal axis, at least one of the first arm or the second arm being movable with respect to the other between an open position, in which the first arm and the second arm are spaced one from another, and a closed position, in which the first arm and the second arm are brought closer together; and
an actuation mechanism arranged at the proximal end of at least one of the first arm or the second arm for moving the first arm and second arm between the open position and the closed position, wherein the actuation mechanism comprises at least a first finger loop arranged at the proximal end of the first arm;
wherein the first finger loop is further arranged to pivotably rotate about the longitudinal axis of the first arm.

2. The handle of claim 1, wherein the first finger loop is arranged to pivot via a hinged connection.

3. The handle of claim 1, wherein the actuation mechanism further comprises a second finger loop arranged at the proximal end of the second arm, the second finger loop being arranged to pivotably rotate about the longitudinal axis of the second arm.

4. The handle of claim 3, wherein the first finger loop arranged at the proximal end of the first arm pivots between a first fixed range of motion and the second finger loop arranged at the proximal end of the second arm pivots between a second fixed range of motion.

5. The handle of claim 4, wherein the first fixed range of motion is between 60 and −60 degrees, and the second fixed range of motion is between 45 and −45 degrees.

6. The handle of claim 4, wherein the first fixed range of motion is between 45 and −45 degrees, and the second fixed range of motion is between 30 and −30 degrees.

7. The handle of claim 4, wherein the first fixed range of motion is between 30 and −30 degrees, and the second fixed range of motion is between 15 and −15 degrees.

8. The handle of claim 1, wherein the first finger loop is configured to pivot about the longitudinal axis of the first arm in both a clockwise and an anticlockwise direction.

9. The handle of claim 8, wherein the first finger loop is configured to pivot about the longitudinal axis of the first arm within a fixed range of motion.

10. The handle of claim 9, wherein the fixed range of motion is between 90 degrees and −90 degrees.

11. The handle of claim 9, wherein the fixed range of motion is between 60 degrees and −60 degrees.

12. The handle of claim 9, wherein the fixed range of motion is between 45 degrees and −45 degrees.

13. The handle of claim 9, wherein the fixed range of motion is between 30 degrees and −30 degrees.

14. The handle of claim 1, wherein a switch mechanism is located on the handle, comprising:
an activation button operable to deliver a source of radio frequency (RF) energy to an end effector disposed on the distal end of at least one of the first arm or the second arm; and
a protrusion operable to compress the activation button.

15. The handle of claim 14, wherein the switch mechanism is arranged on the handle such that, the activation button is configured to be activated by one of the first arm or the second arm when the handle is in the closed position.

16. A surgical instrument, comprising:
an end effector; and
a handle for actuating the end effector according to claim 1.

17. The surgical instrument of claim 16, wherein the end effector comprises a first jaw member disposed on the distal end of the first arm and a second jaw member disposed on the distal end of the second arm.

18. An electrosurgical system, comprising:
an RF electrosurgical generator; and
a surgical instrument according to claim 16.

19. The handle of claim 1, further comprising a blade trigger and a slot configured to receive the blade trigger.

* * * * *